(12) United States Patent
Fujii et al.

(10) Patent No.: US 11,172,982 B2
(45) Date of Patent: Nov. 16, 2021

(54) INTEGRATED GROUNDING ELECTRODES FOR ELECTROCAUTERY VESSEL HARVESTER

(71) Applicant: TERUMO CARDIOVASCULAR SYSTEMS CORPORATION, Ann Arbor, MI (US)

(72) Inventors: Tatsunori Fujii, Bear, DE (US); Safi Siddiqui, Chestertown, MD (US); Randal J. Kadykowski, South Lyon, MI (US)

(73) Assignee: TERUMO CARDIOVASCULAR SYSTEMS CORPORATION, Ann Arbor, MI (US)

( * ) Notice: Subject to any disclaimer, the term of this patent is extended or adjusted under 35 U.S.C. 154(b) by 520 days.

(21) Appl. No.: 16/026,156

(22) Filed: Jul. 3, 2018

(65) Prior Publication Data

US 2020/0008866 A1     Jan. 9, 2020

(51) Int. Cl.
*A61B 18/14* (2006.01)
*A61B 18/16* (2006.01)
*A61B 18/00* (2006.01)

(52) U.S. Cl.
CPC .......... *A61B 18/1482* (2013.01); *A61B 18/16* (2013.01); *A61B 2018/00428* (2013.01); *A61B 2018/00595* (2013.01); *A61B 2018/00601* (2013.01); *A61B 2018/00982* (2013.01); *A61B 2018/162* (2013.01)

(58) Field of Classification Search
None
See application file for complete search history.

(56) References Cited

U.S. PATENT DOCUMENTS

| | | | |
|---|---|---|---|
| 5,967,971 A | 10/1999 | Bolser | |
| 6,086,586 A * | 7/2000 | Hooven | A61B 18/1442 606/48 |
| 6,193,653 B1 | 2/2001 | Evans et al. | |
| 6,296,640 B1 | 10/2001 | Wampler et al. | |
| 6,432,044 B1 | 8/2002 | Lunsford et al. | |

(Continued)

OTHER PUBLICATIONS

VirtuoSaph™ Endoscopic Vein Harvesting System, Clinical Overview, Terumo, 2008.

(Continued)

*Primary Examiner* — Ronald Hupczey, Jr.
(74) *Attorney, Agent, or Firm* — Darryl Newell; MacMillan, Sobanski & Todd, LLC (57) ABSTRACT

An endoscopic vessel harvester cuts and cauterizes side branches from a target vessel using a cutter member that extends at a distal end of an insertion member. The cutter member has a plate defining a slit for receiving a side branch. A cutting electrode is disposed at a base of the slit and a pair of grounding electrodes are each mounted to an outer surface of the plate on opposite sides of the slit. Each grounding electrode has a raised longitudinal ridge adjoining a portion of the slit including the base of the slit and has a spot cautery wing extending laterally away from the slit with a surface configured to engage a surface of the tunnel. The longitudinal ridges each have an upright jamb surface configured to contact the side branch remotely from the cutting electrode so that it is unnecessary to make a grounding contact on the tunnel.

8 Claims, 11 Drawing Sheets

(56) References Cited

U.S. PATENT DOCUMENTS

| | | | |
|---|---|---|---|
| 6,468,275 B1 | 10/2002 | Wampler et al. | |
| 6,471,638 B1 | 10/2002 | Chang et al. | |
| 7,316,683 B2 | 1/2008 | Kasahara et al. | |
| 7,326,178 B1 | 2/2008 | Lunsford et al. | |
| 7,331,971 B2 | 2/2008 | Kasahara et al. | |
| 7,476,198 B1 | 1/2009 | Chin et al. | |
| 7,850,687 B2 | 12/2010 | Kasahara | |
| 8,460,331 B2 | 6/2013 | Chin | |
| 8,465,488 B2 * | 6/2013 | Maeda | A61B 18/148 606/46 |
| 8,702,700 B2 * | 4/2014 | Maeda | A61B 18/1482 606/46 |
| 8,932,208 B2 | 1/2015 | Kendale et al. | |
| 9,402,679 B2 | 8/2016 | Ginnebaugh et al. | |
| 2006/0206112 A1 | 9/2006 | Kasahara | |
| 2008/0208191 A1 | 8/2008 | Kadykowski | |
| 2008/0249556 A1 | 10/2008 | Kamatani | |
| 2010/0292533 A1 | 11/2010 | Kasahara et al. | |
| 2012/0010463 A1 | 1/2012 | Chin et al. | |
| 2012/0035606 A1 | 2/2012 | Kano et al. | |
| 2013/0274548 A1 | 10/2013 | Feis et al. | |
| 2013/0282009 A1 | 10/2013 | Knodel | |
| 2014/0378957 A1 | 12/2014 | Orphanos et al. | |
| 2015/0142041 A1 | 5/2015 | Kendale et al. | |
| 2015/0164488 A1 | 6/2015 | Stewart | |
| 2017/0056038 A1 | 3/2017 | Hess et al. | |
| 2017/0347996 A1 | 12/2017 | Lau et al. | |
| 2018/0000470 A1 | 1/2018 | Willis et al. | |

OTHER PUBLICATIONS

VirtuoSaph® Plus, Endoscopic Vessel Harvesting System, Harvesting a New Standard of Care, Terumo, 2010.

* cited by examiner

INTEGRATED GROUNDING ELECTRODES FOR ELECTROCAUTERY VESSEL HARVESTER

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to endoscopic harvesting of blood vessels, and, more specifically, to grounding electrodes for contacting tissue to electrically cut and cauterize branch vessels and associated tissues.

In connection with coronary artery bypass grafting (CABG), a blood vessel or vessel section, such as an artery or vein, is "harvested" (i.e., removed) from its natural location in a patient's body and to use it elsewhere in the body. In CABG surgery, the blood vessel is used to form a bypass between an arterial blood source and the coronary artery that is to be bypassed. Among the preferred sources for the vessel to be used as the bypass graft are the saphenous veins in the legs and the radial artery in the arms.

Endoscopic surgical procedures for harvesting a section of a vein (e.g., the saphenous vein) subcutaneously have been developed in order to avoid disadvantages and potential complications of harvesting through a continuous incision (e.g., along the leg) for the full length of the desired vessel section in order to provide adequate exposure for visualizing the vessel and for introducing surgical instruments to sever, cauterize and ligate the tissue and side branches of the vessel. One such minimally-invasive technique employs a small incision for locating the desired vessel and for introducing one or more endoscopic harvesting devices. Primary dissection occurs by introduction of a dissecting instrument through the incision to create a working space and separate the vessel from the surrounding tissue. Then a cutting instrument is introduced into the working space to sever the blood vessel from the connective tissue surrounding the section to be harvested and any side branches of the blood vessel. The branches may be clipped and/or cauterized.

An example of a commercially available product for performing the endoscopic vessel harvesting described above is the VirtuoSaph Plus™ Endoscopic Vein Harvesting System from Terumo Cardiovascular Systems Corporation of Ann Arbor, Mich. Endoscopic vessel harvesting systems are also shown in U.S. Pat. No. 7,331,971 and U.S. published application 2010/0292533A1, which are incorporated herein by reference in their entirety.

In the VirtuoSaph™ System, the cutting tool for severing and cauterizing branches has the form of a V-cutter wherein a V-shaped tip at the distal end of the cutter guides a branch to be cut into a longitudinal slit. Electrodes are electrically energized with a high current, high voltage signal at a high frequency in order to sever and cauterize the branch by extreme heating.

In one typical procedure, the endoscopic entry site is located near the midpoint of the vessel being harvested, with dissection and cutting of branches proceeding in both directions along the vessel from the entry site. In order to remove the desired section of the blood vessel, a second small incision, or stab wound, is made at one end thereof and the blood vessel section is ligated. A third small incision is made at the other end of the blood vessel section which is then ligated, thereby allowing the desired section to be completely removed through the first incision. Alternatively, only the first two incisions may be necessary if the length of the endoscopic device is sufficient to obtain the desired length of the blood vessel while working in only one direction along the vessel from the entry point.

A trocar is placed in the entry site, and an elongated, blunt dissector is inserted into the patient (e.g., the patient's leg) via the trocar. An endoscopic viewer is removably attached to the dissector. The dissector carries a gas channel for delivering an insufflation gas, such as carbon dioxide gas, to inflate a tunnel as dissection progresses. Under observation by this endoscope inserted near the knee, and sequentially working along the saphenous vein in two opposite directions (i.e., from the knee to the groin and then from the knee to the ankle), the desired portion of the vein is separated and isolated from its surrounding tissue together with multiple small venous branches from the desired vein portion.

Next, the dissector is removed from the leg interior, and in its place the surgeon or medical technician inserts a harvesting tool into the leg via the trocar. The endoscope is removably attached to the harvesting tool, which is also provided with a channel for a fluid such as, for example, carbon dioxide gas. A blood-vessel holder is retractably provided at the tip of the tool along with a retractable blood-vessel cutter/cauterizer. Forward and backward movement of the blood-vessel holder along the target vessel are made feasible by a blood-vessel holder manipulation member on a handle provided at the proximal end of the harvesting tool which is outside the trocar.

While observing the desired portion of vein via the endoscope, the blood-vessel holder is guided along the vein which has been captured in the blood-vessel holder. Multiple venous branches protruding from the desired portion of vein are sequentially cut by use of the blood-vessel cutter, working from the knee to the groin and then from the knee to the ankle. The blood-vessel cutter is configured so as to simultaneously cut and cauterize branch vessels by means of application of a high-frequency current to generate extreme heat in a very localized area. The conventional cutter tip possesses a slit with a V-shaped opening. A cutting electrode resides at the base of the slit for contacting a branch vessel. In order to establish a complete electrical circuit, two grounding electrodes have been disposed on opposite sides of the slit. The grounding electrodes are arranged to contact tissue at the tunnel wall and have a larger surface area than the cutting electrode so that the electrical energy is most highly concentrated at the cutting electrode. After a branch is captured at the base end of the slit against the cutting electrode by advancing the harvesting tool, a high-frequency current is activated between the cutting electrode and the grounding electrodes which induces a high temperature that simultaneously cuts and cauterizes the severed portions of the branch vessel.

When cutting of all the venous branches from the desired portion of vein is completed, incisions are made at the two ends of the desired portion of vein and then the vein is extracted from the central opening.

Favorability of patient outcomes depend in part on the duration of the surgical procedure and the quality of the cutting and cauterizing steps, and these depend in part on the design and operating attributes of the surgical instruments. Therefore, improvements in the instruments that can lead to better patient outcomes are highly desirable. Furthermore, the application of the high-frequency electrical power to the body creates extreme heat which spreads into the body beyond the specific structure being cut and/or cauterized. It would also be desirable to limit the spreading.

SUMMARY OF THE INVENTION

In one aspect of the invention, an endoscopic vessel harvester comprises a longitudinal insertion member with a distal end adapted for insertion into a tunnel dissected along a target vessel within a body of a patient. A vessel keeper is extendably mounted at the distal end of the insertion member comprising a capture frame with an opened position to admit the target vessel and having a closed position to slidably capture the target vessel. A cutter member is extendably mounted at the distal end of the insertion member comprising a plate defining a slit for receiving a side branch to the target vessel. A cutting electrode is disposed at a base of the slit and a pair of grounding electrodes are each mounted to an outer surface of the plate on opposite sides of the slit. Each grounding electrode has a raised longitudinal ridge adjoining a portion of the slit including the base of the slit and has a spot cautery wing extending laterally away from the slit with a surface configured to engage a surface of the tunnel. The longitudinal ridges each have an upright jamb surface configured to contact the side branch remotely from the cutting electrode. Preferably, each upright jamb surface has a height of 0.5 mm or greater.

DETAILED DESCRIPTION OF PREFERRED EMBODIMENTS

Figure 1:
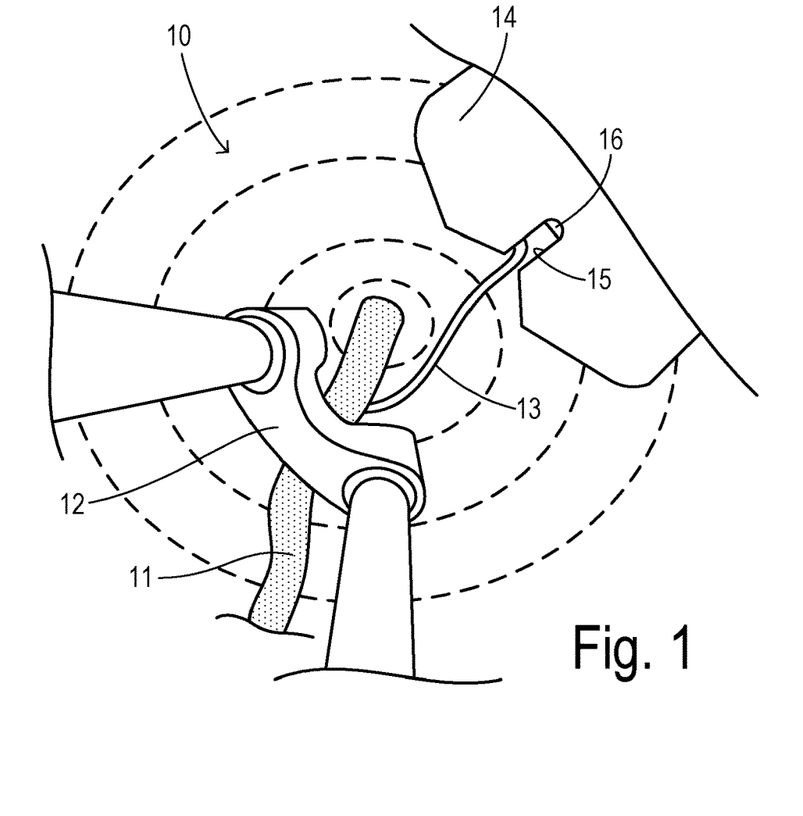
FIG. 1 is an endoscopic view showing a side branch being captured in a slit of a cutter member.

FIG. 1 shows an endoscopic view from a vessel harvesting system wherein a tunnel 10 has been dissected around a target vessel 11 by blunt dissection as known in the art. A vessel keeper includes a frame 12 having an opening that captures vessel 11. A side branch 13 extends from vessel 11 to a wall of tunnel 10, and branch 13 must be cut and cauterized as part of preparing vessel 11 for removal from the body.

Figure 2:
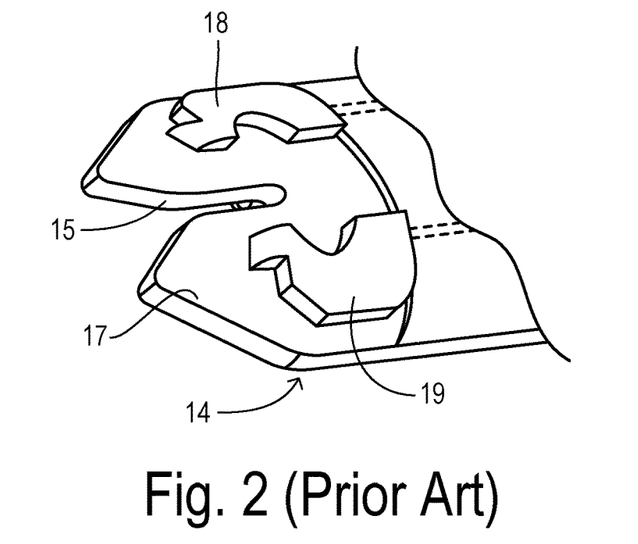
FIG. 2 is a perspective view of a V-tip of a prior art cutter.
Figure 3:
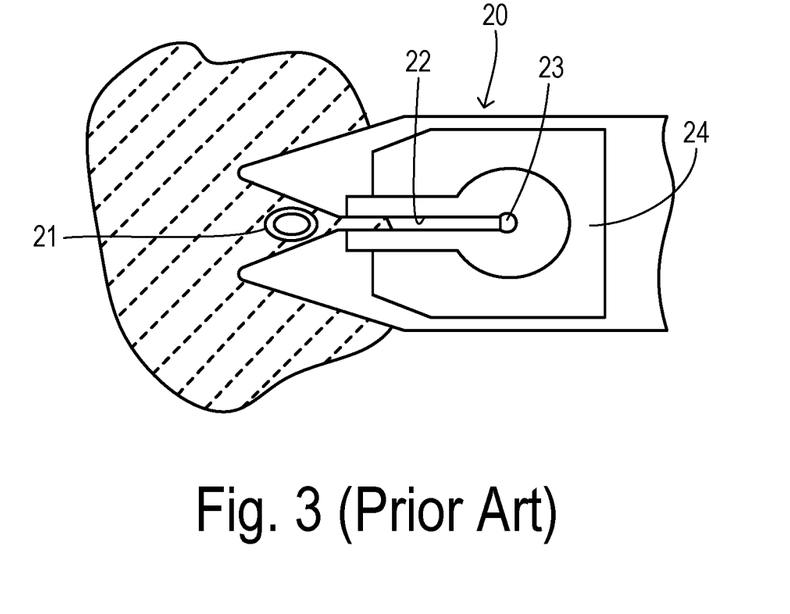
FIGS. 3 and 4 are top views showing a side branch advancing into the slit of a prior art cutter.
Figure 4:
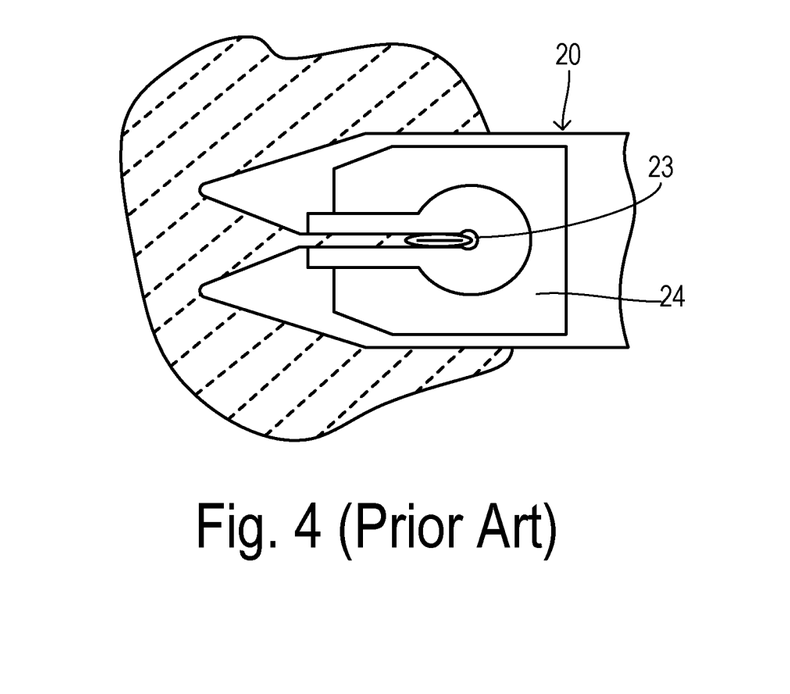

A vessel cutter member 14 is shown extending toward branch 13 in order to capture it in a slit 15. Cutter 14 has a cutter electrode 16 at a base of slit 15. An outer (tunnel-facing) side of cutter 14 is shown in FIG. 2. Cutter 14 is formed by a plate 17 carrying grounding electrodes 18 and 19. FIGS. 3 and 4 show an alternate design of a vessel cutter tip 20 with a side branch 21 advancing in a slit 22. Side branch 21 may be compressed as it traverses slit 22 until coming into contact with a cutting electrode 23 at the base of slit 22. A grounding electrode 24 is spaced away from slit 22 and is arranged to contact the surface of the tunnel in order to establish electrical continuity so that the vessel to be cut and cauterized forms part of an electrical circuit path between electrodes 23 and 24.

Figure 5:
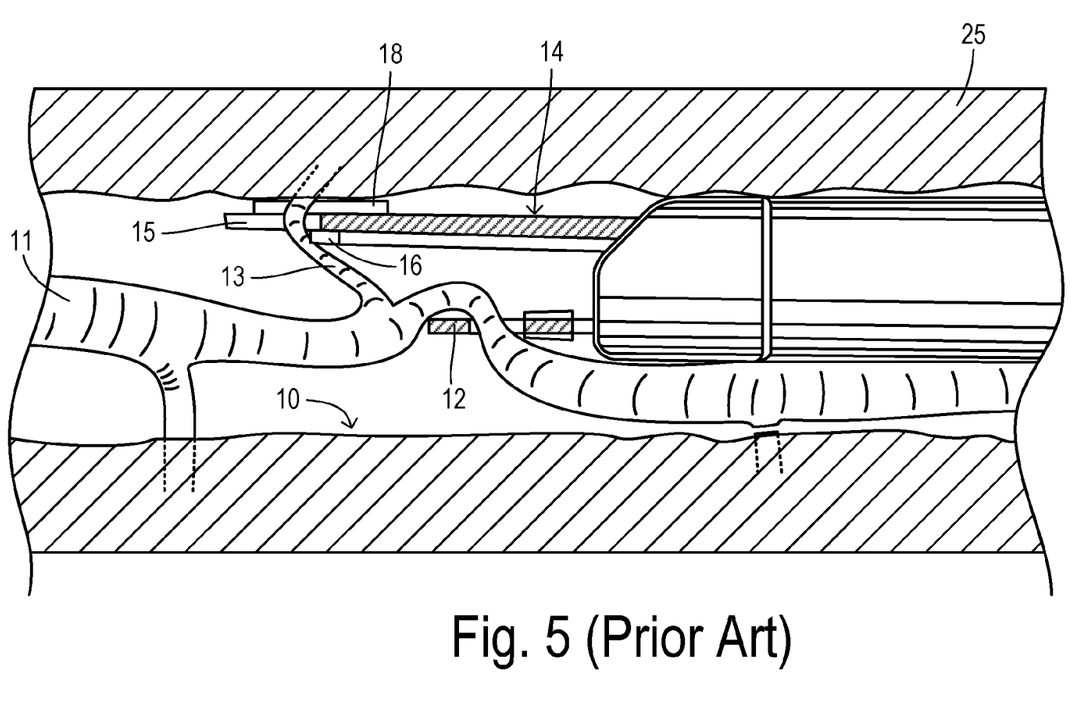
FIGS. 5 and 6 are side views in partial cross section showing placement of the grounding electrodes of a prior art cutter against a dissected tunnel.
Figure 6:
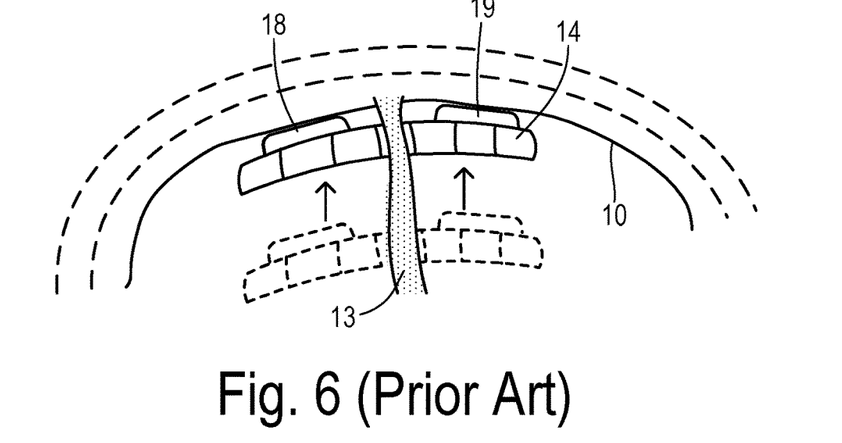

FIG. 5 shows an insertion member or sleeve 25 of an endoscopic vessel harvester inserted into tunnel 10 and carrying vessel holder 12 and cutter member 14. In order to establish a completed electrical circuit, branch 13 contacts cutting electrode 16 at the same time that grounding electrode 18 contacts a wall of tunnel 10. As shown in FIG. 6, branch 13 is typically initially captured within slit 15 in a region close to vessel 11 and is then moved outwardly in order to obtain contact between the grounding electrodes and tunnel 10 while keeping branch 13 within slit 15. Besides requiring additional time and effort, the need for placement against the tunnel wall increases the region of thermal exposure and thermal spreading to include more than just the branch being cut and cauterized.

Figure 7:
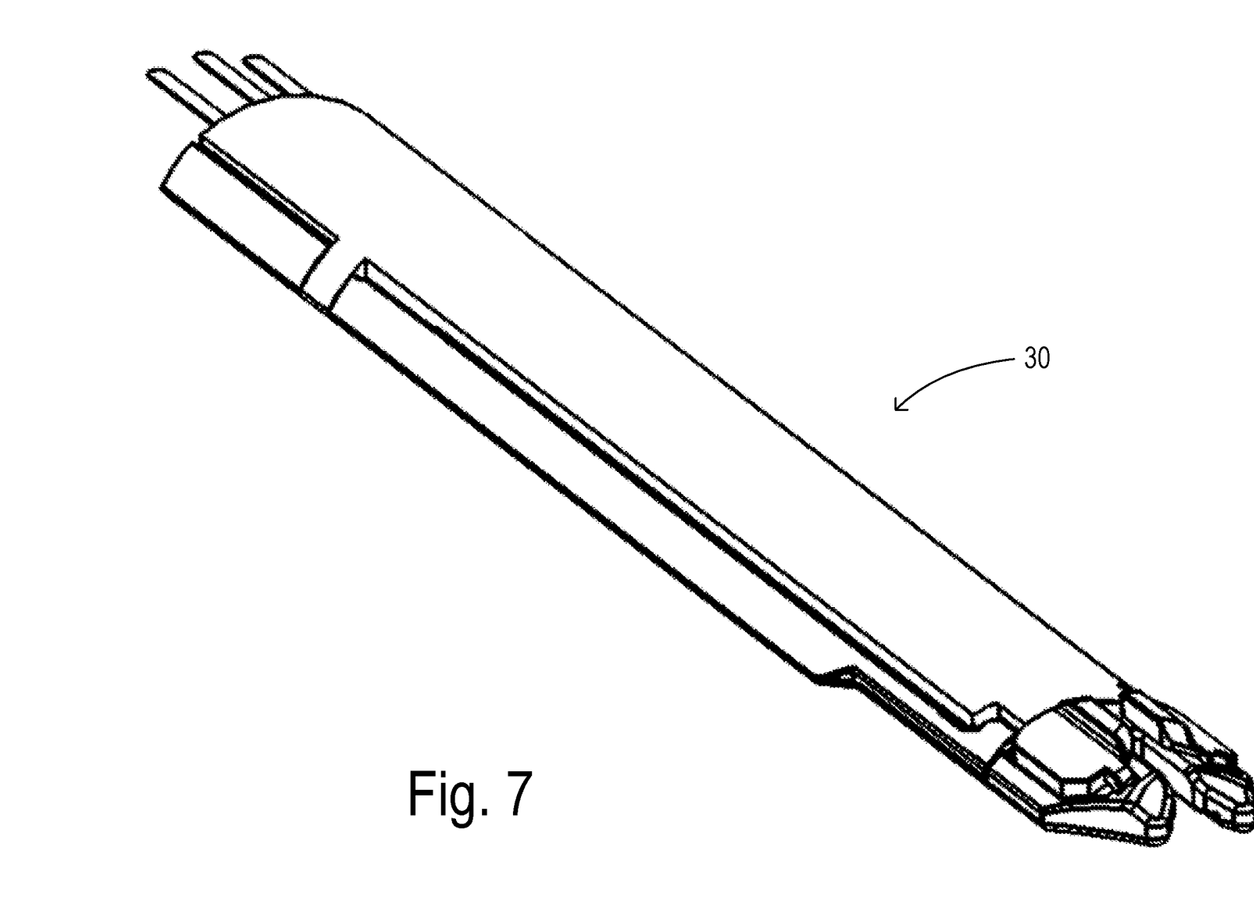
FIG. 7 is a perspective view of an extendable cutter according to one embodiment of the invention.
Figure 8:
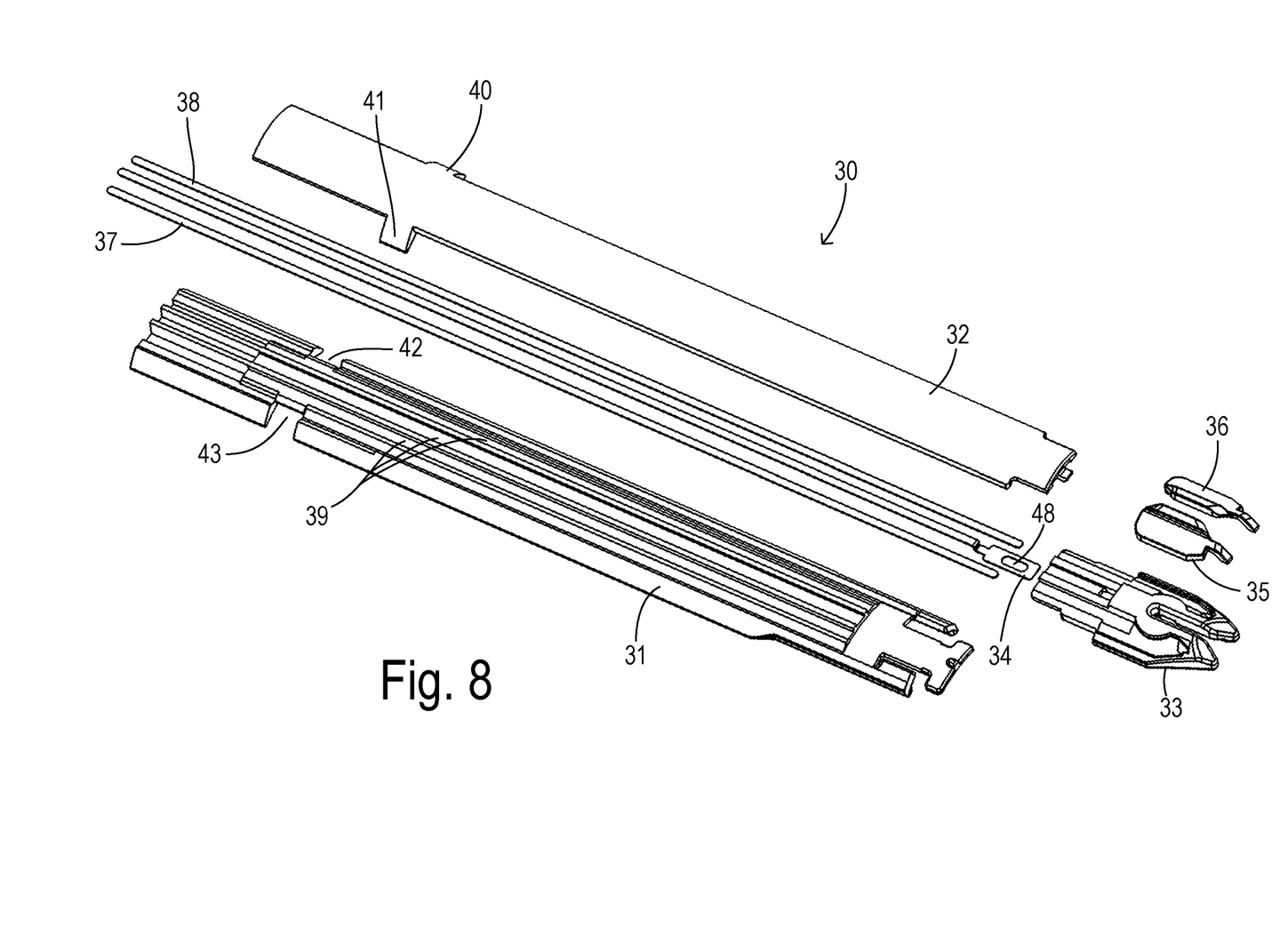
FIGS. 8 and 9 are exploded views of the cutter of FIG. 7.
Figure 9:
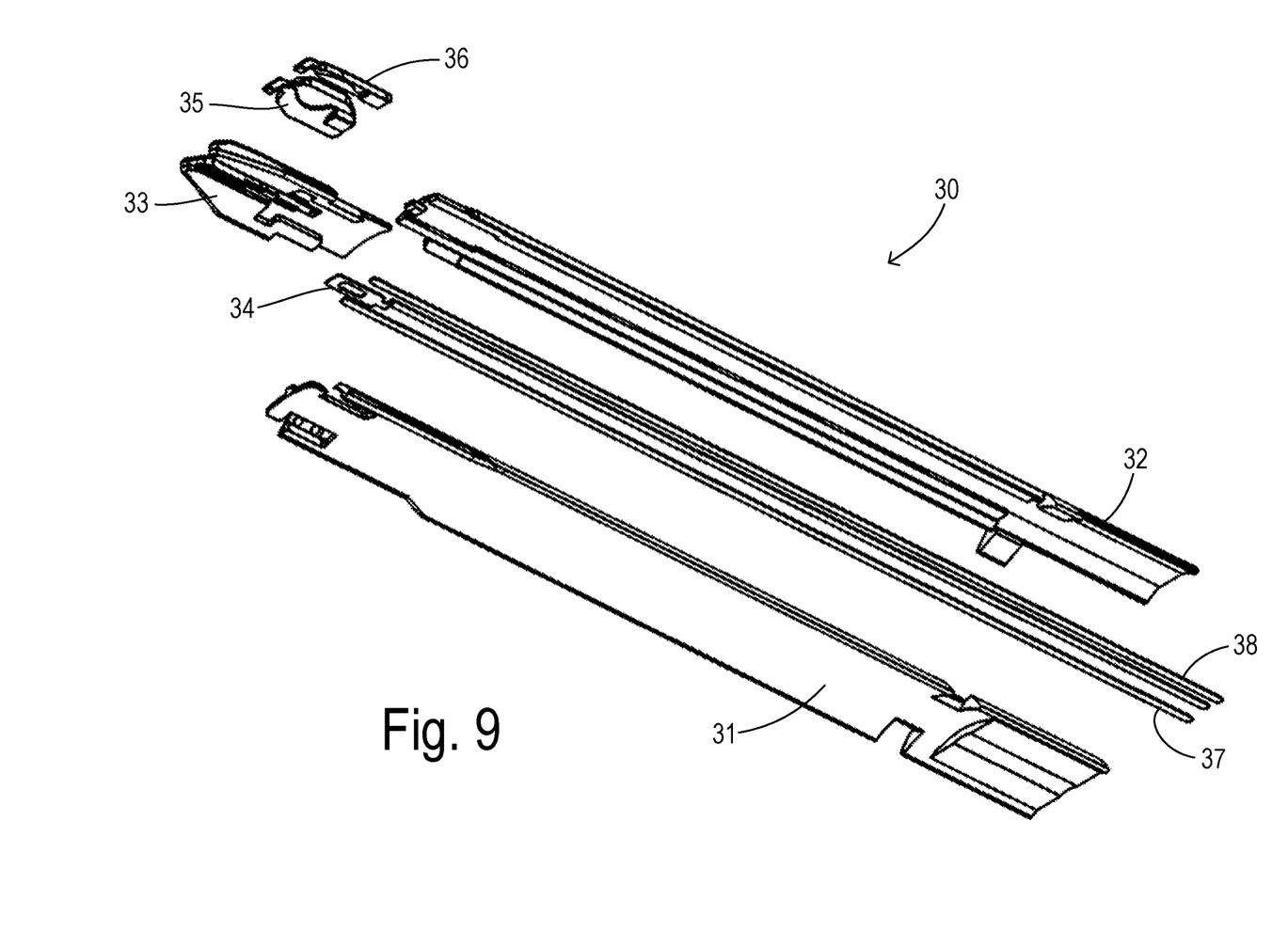

To reduce time and effort and to further limit thermal spreading beyond the branch vessel being cut and cauterized, the present invention provides improved grounding electrodes in a cutter member 30 shown in FIGS. 7-9. Cutter member 30 is extendable from the longitudinal insertion member of an endoscopic vessel harvesting tool, such as the VirtuoSaph Plus™ product noted above. Cutter member 30 is constructed of a lower sheath 31, an upper sheath 32, a cutter tip 33, an active cutting electrode 34, grounding electrodes 35 and 36, and ground electrode extensions 37 and 38. Lower sheath 31 includes slots 39 for receiving electrode 34 and extensions 37 and 38. Tabs 40 and 41 of upper sheath 32 fit into corresponding notches 42 and 43 in lower sheath 31. Sheaths 31 and 32 can be fabricated from a molded polycarbonate.

Figure 10:
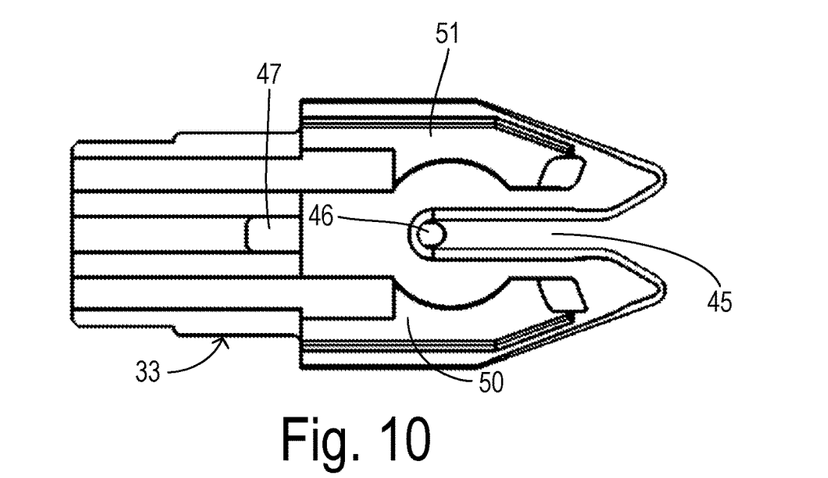
FIGS. 10 and 11 are top plan and front perspective views of a partial assembly of the cutter of FIG. 7.
Figure 11:
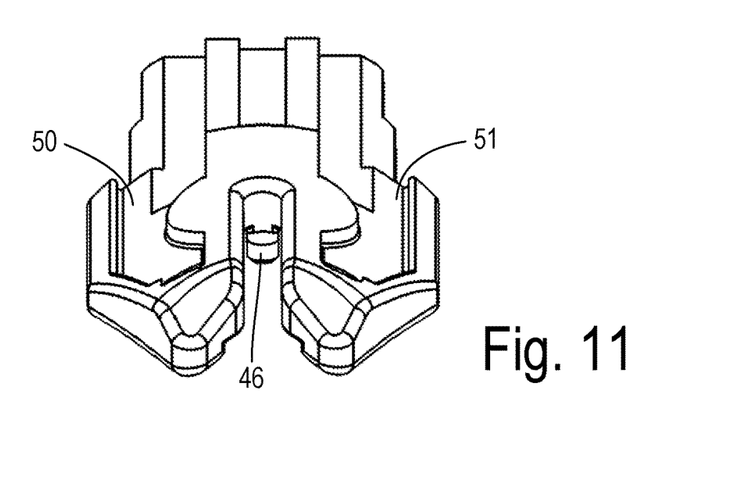

Tip 33 is shown in greater detail in FIGS. 10 and 11. It is preferably formed of a ceramic material and can be joined to the sheaths using a high temperature RTV silicone adhesive. A distal slot 45 divides a distal end of tip 33 into left and right wing sections having recesses 50 and 51 for receiving the ground electrodes. A tab 46 extends from a main body of tip 33 at the bottom of slit 45 in order to receive an opening 48 in the end of active cutting electrode 34. An opening 47 is disposed in tip 33 to allow a portion of active cutting electrode 34 to pass from the bottom side of tip 33 to the top side between the upper and lower sheaths.

Figure 12:
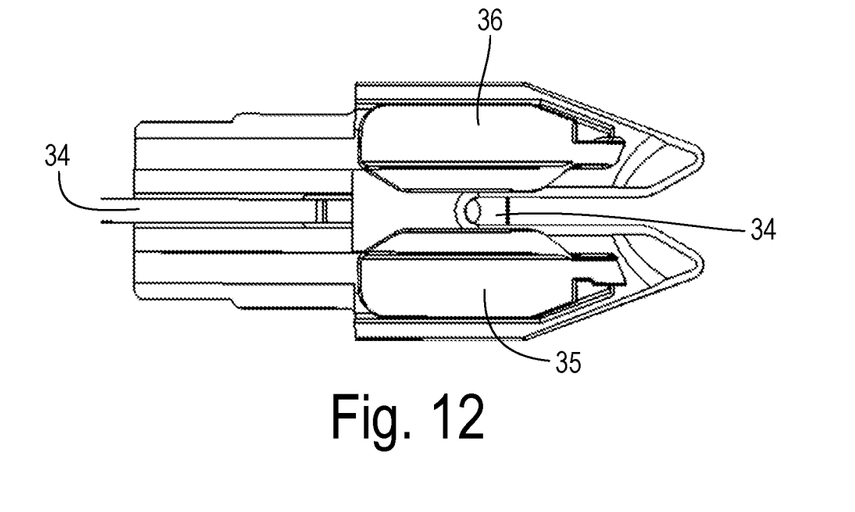
FIGS. 12 and 13 are top plan and front perspective views of the partial assembly of FIGS. 10 and 11 with the cutter electrode added.
Figure 13:
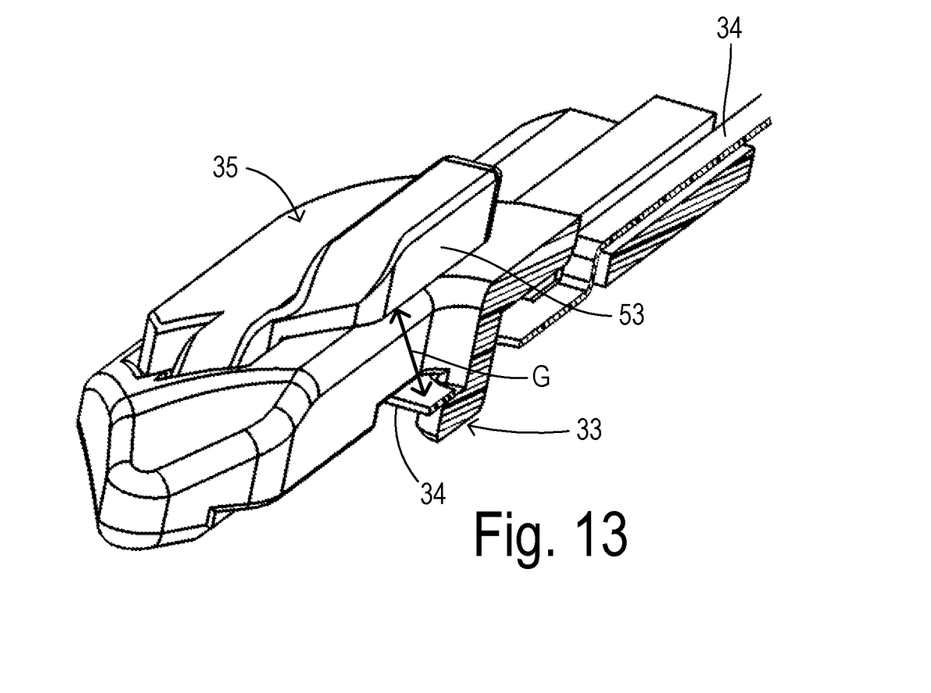

FIGS. 12 and 13 show tip 33 after assembly of active electrode 34 and grounding electrodes 35 and 36. Grounding electrodes 35 and 36 are symmetrical about slit 34 and may each include a forward nose extension captured in matching features in respective recesses 50 and 51. In addition, grounding electrodes 35 and 36 may be retained within recesses 50 and 51 by welding them to the electrode extensions and/or by use of adhesives. FIG. 13 illustrates a gap G between a forward edge of active electrode 34 and an upright jamb surface 53 which provides a branch grounding surface. When a branch vessel is in contact with electrode 34 and jamb grounding surface 53 and the high-frequency power signal is applied, then the electrocautery heating is applied only to the branch being cauterized so that less heat spreads to the tunnel or surrounding structures.

Figure 14:
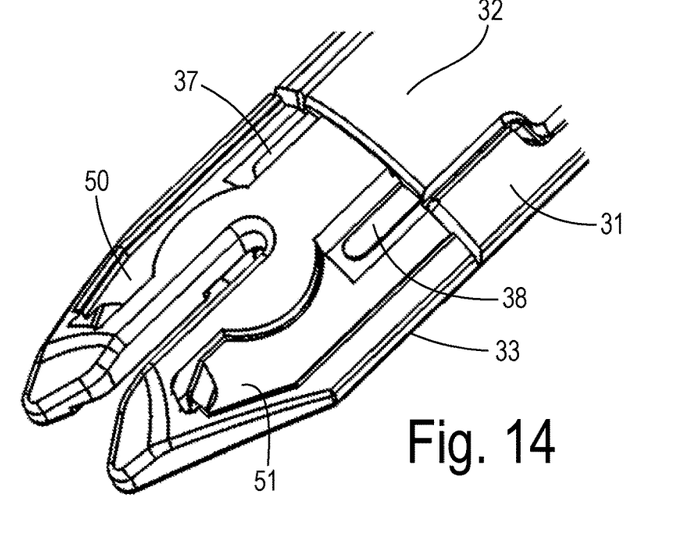
FIG. 14 is a perspective view of the tip of the cutter with the grounding electrodes removed.
Figure 15:
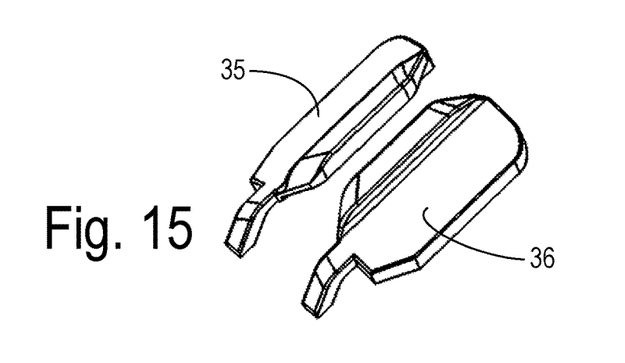
FIG. 15 is a perspective view of the grounding electrodes.
Figure 16:
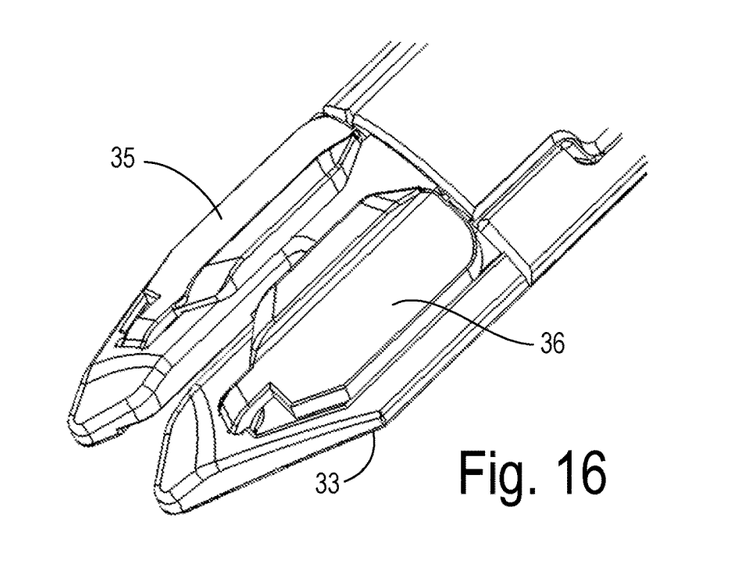
FIG. 16 is a perspective view of the tip of the cutter of FIG. 14 with the grounding electrodes added.

FIG. 14 shows a distal end of cutter member 30 with electrode extensions 37 and 38 protruding from lower and upper sheaths 31 and 32 so that they are exposed within recesses 50 and 51. Grounding electrodes 35 and 36 as shown in FIG. 15 are placed into recesses 50 and 51 as shown in FIG. 16. Electrodes 35 and 36 are welded for electrical continuity to extensions 37 and 38 thereby allowing independent switching of ground electrodes 35 and 36 to the bipolar high-frequency power source. For cutting/cauterizing a branch, one side of the power source is applied to cutting electrode 34 and the other side of the power source is applied to grounding electrodes 35 and 36 simultaneously. For spot cautery of surfaces (e.g., the tunnel surface), one side of the power source is applied to grounding electrode 35 and the other side of the power source is applied to grounding electrode 36.

Figure 17:
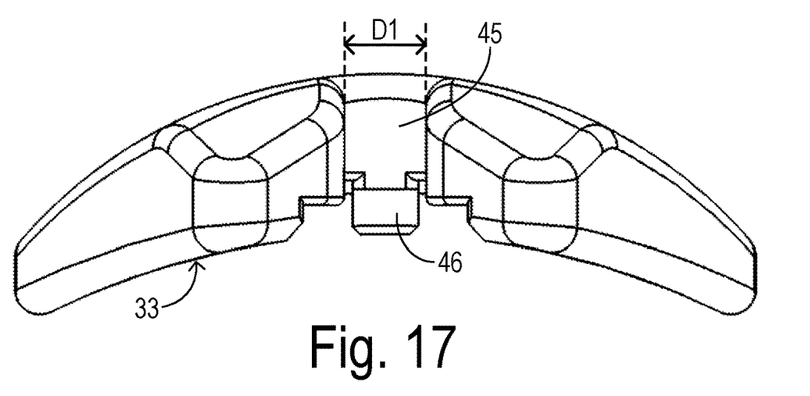
FIGS. 17 and 18 are front plan views of the tip of the cutter without and with the electrodes, respectively.

FIG. 17 shows a front view of tip 33 looking into slot 45 toward 46. Slit 45 defines a width D1 which is adapted to accommodate entry of a range of branch vessel sizes into slit 45. Distance D1 may preferably be about 1.0 mm and a longitudinal depth of slit 45 may be about 10 mm.

Figure 18:
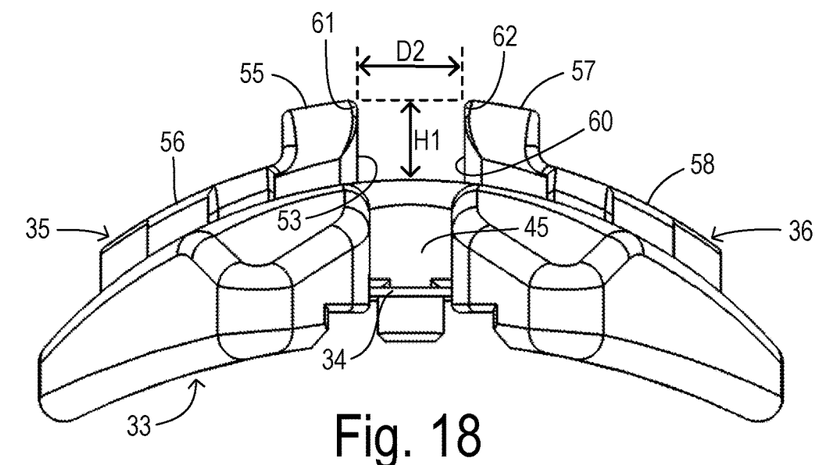

FIG. 18 is a front view of tip 33 with active electrode 34 and grounding electrodes 35 and 36 installed. Ground electrode 35 has a raised longitudinal ridge 55 and a spot cautery wing 56. Ground electrode 36 has a raised longitudinal ridge 57 and a spot cautery wing 58. Ridges 55 and 57 define i) a grounding electrode spacing D2 which is greater than or equal to D1 and ii) a height H1 extending above slit 45. Preferably, distance D2 is slightly greater than or equal to distance D1.

Ridges 55 and 57 define upright jamb surfaces 53 and 60 configured to contact the side branches where they exit slit 45 (i.e., at a spot remote from cutting electrode 34). Jamb surfaces 53 and 60 are substantially parallel with each other and with the sides of slit 45. Preferably, each upright jamb surface 53 and 60 is located within 0.3 mm of an upright profile of slit 45 (i.e., each is within 0.3 mm of an imaginary parallel plane that extends up from the sides of slit 45 such that distance D2 is no more than 0.6 mm greater than distance D1). Height H1 of upright jamb surfaces 53 and 60 is preferably about 0.5 mm or greater.

Raised ridges 55 and 57 have upper corners or edges 61 and 62 along the top of jamb surfaces 53 and 60 which are curved to avoid any sharp edges that could damage the side branches or other tissues during manipulation of the harvester tool. Preferably, edges 61 and 62 have a radius of at least 0.1 mm.

Figure 19:
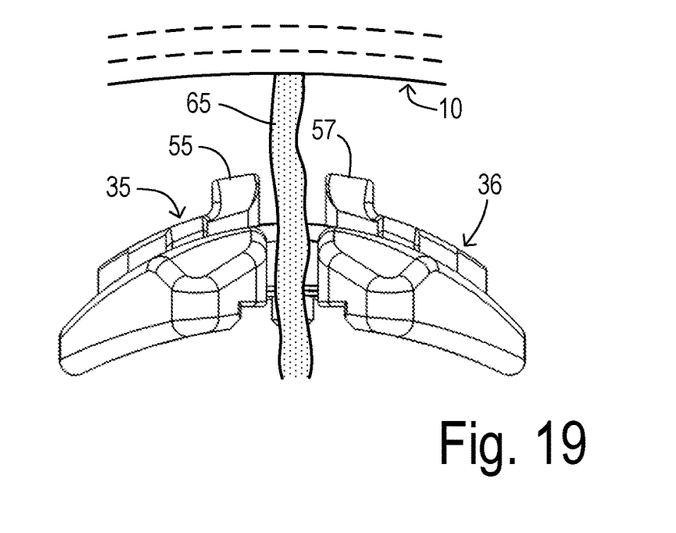
FIGS. 19 and 20 are front views of the cutter tip receiving a branch vessel, wherein the tip is pivoted to obtain grounding contact with a grounding electrode.
Figure 20:
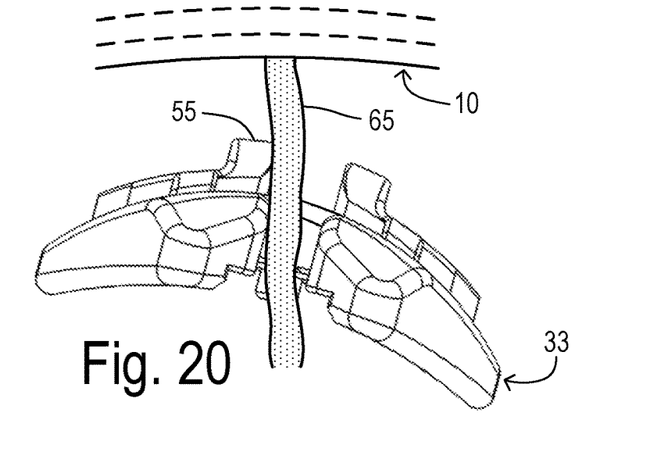

When a side branch vessel is being cut which has a diameter equal to or greater than separation distance D2 between electrodes 35 and 36, then a sufficient grounding contact will automatically be made with the branch vessel. In the event of a side branch having a diameter less than D2, then a pivoting or rolling motion of the insertion member can ensure sufficient contact as shown in FIGS. 19 and 20. Thus, a branch vessel 65 is shown having a diameter less than the slit width so that it contacts neither one of raised ridges 55 or 57. By pivoting the insertion member as shown in FIG. 20, cutter member 33 and its attached structures rotate until vessel 65 makes good contact with raised ridge 55. The degree of movement is much less than having to relocate to the wall surface of tunnel 10, and the application of cauterizing heat is still restricted to branch vessel 65 rather than being applied directly to tunnel 10.

Figures 21, 22, 23:
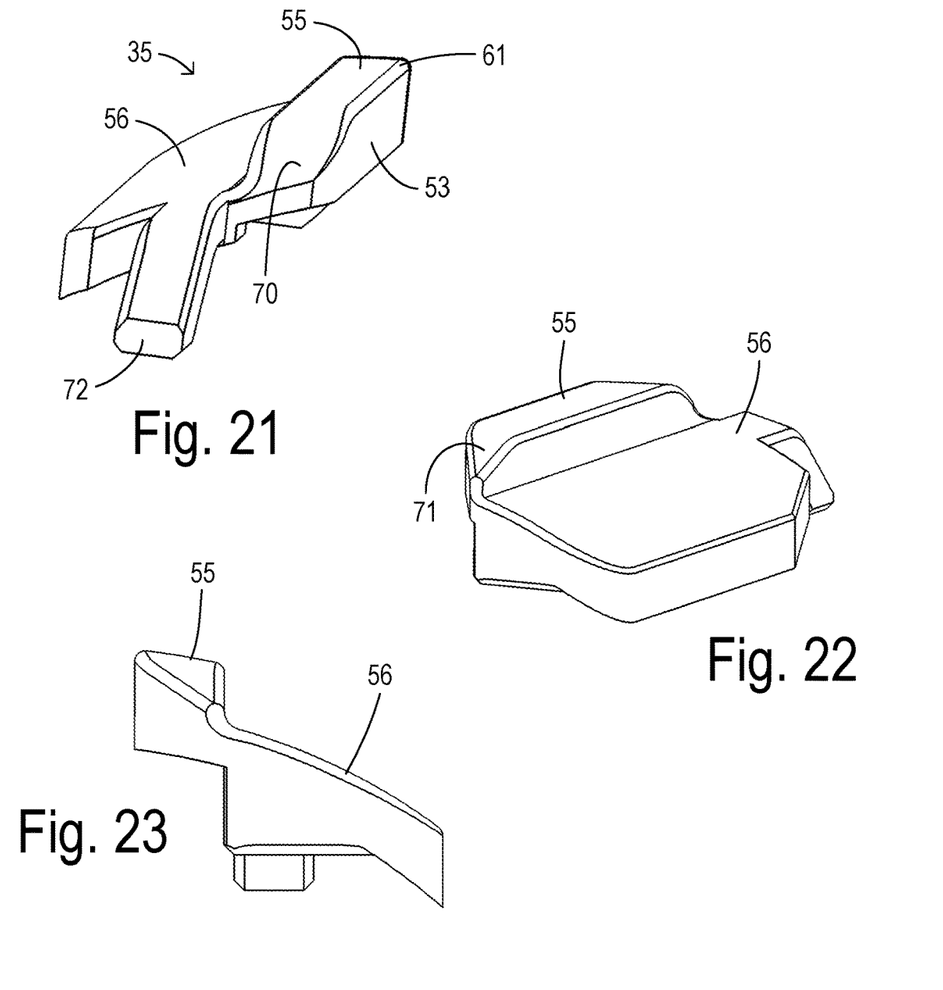
FIG. 21 is a front, perspective view of a grounding electrode in greater detail.
FIG. 22 is a side, perspective view of the grounding electrode of FIG. 21.
FIG. 23 is a rear view of the grounding electrode of FIG. 21.

FIGS. 21-23 show grounding electrode 35 in greater detail. In order to obtain smooth movement within the tunnel, raised ridge 55 has a ramped leading edge 70 and a ramped trailing edge 71. Forward nose 72 fits into a corresponding portion of the recess within the tip for positively retaining electrode 35. Spot cautery wing 56 extends laterally away from raised ridge 55 (laterally away from the slit) to provide a surface configured to engage the tunnel surface when it is desired to perform spot cautery by energizing a signal between the grounding electrodes. Preferably, spot cautery wing 56 defines a curved planar surface as shown in FIGS. 21-23 to easily conform to the tunnel surface and to optimize the contact interface with the tissues at the tunnel wall so that a desired region can be spot cauterized. A preferred material for the electrodes is stainless steel or other biocompatible materials such as titanium which can be fabricated by metal injection molding.

What is claimed is:

1. An endoscopic vessel harvester comprising:
   a longitudinal insertion member having a distal end adapted for insertion into a tunnel dissected along a target vessel within a body of a patient;
   a vessel keeper extendably mounted at the distal end of the insertion member comprising a capture frame with an opened position to admit the target vessel and having a closed position to slidably capture the target vessel; and
   a cutter member extendably mounted at the distal end of the insertion member comprising a plate defining a slit for receiving a side branch to the target vessel, a cutting electrode disposed at a base of the slit, and a pair of grounding electrodes each mounted to an outer surface of the plate on opposite sides of the slit, wherein the slit has sides which are configured to guide the side branch to the cutting electrode, wherein each grounding electrode has a raised longitudinal ridge adjoining a portion of the slit including the base of the slit and has a spot cautery wing extending laterally away from the slit with a surface configured to engage a surface of the tunnel, wherein the longitudinal ridges each have an upright jamb surface configured to contact the side branch remotely from the cutting electrode;
   wherein the upright jamb surfaces are substantially parallel with each other and with the sides of the slit, and wherein the upright jamb surfaces are configured to contact the side branch upon exiting the slit, and wherein the upright jamb surfaces are configured to establish electrical continuity to the side branch so that a high-frequency current between the cutting electrode and the grounding electrodes flows in the side branch and not in the tunnel.

2. The harvester of claim 1 wherein each upright jamb surface has a height of 0.5 mm or greater.

3. The harvester of claim 1 wherein each upright jamb surface is located within 0.3 mm of an upright profile of the slit.

4. The harvester of claim 1 wherein an upper edge of each upright jamb surface has a radius of at least 0.1 mm.

5. The harvester of claim 1 wherein each longitudinal ridge has a ramped leading edge and a ramped trailing edge.

6. The harvester of claim 1 wherein the cutting electrode and the grounding electrodes are comprised of stainless steel.

7. The harvester of claim 1 further comprising:
an electrode extension welded to at least one of the grounding electrodes and extending through the insertion member for connecting to a bipolar power source.

8. The harvester of claim 1 wherein the surface of each spot cautery wing defines a curved planar surface for contacting the tunnel.

* * * * *